United States Patent [19]

Lowrie et al.

[11] Patent Number: 4,554,359

[45] Date of Patent: Nov. 19, 1985

[54] 3-SUBSTITUTED PENTANEDIOIC ACIDS AND DERIVATIVES THEREOF

[75] Inventors: Harman S. Lowrie, Northbrook; John S. Baran, Winnetka, both of Ill.

[73] Assignee: G. D. Searle & Co., Skokie, Ill.

[21] Appl. No.: 569,007

[22] Filed: Jan. 9, 1984

[51] Int. Cl.$^4$ .................... C07D 309/10; C07C 59/01; C07C 69/675
[52] U.S. Cl. .................................. 549/231; 560/126; 560/180; 562/508; 562/582; 562/599
[58] Field of Search ............... 549/231; 560/126, 180; 562/508, 582

[56] References Cited

U.S. PATENT DOCUMENTS 3,818,080 6/1974 Baran et al. .................... 562/508 X Primary Examiner—Richard L. Raymond
Attorney, Agent, or Firm—John J. McDonnell

[57] ABSTRACT

This invention relates to methods of preventing or reducing the degradation of elastin and other proteins and thereby preventing or retarding the disease states caused by said degradation by administering compounds of the formula:

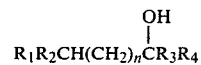

or their pharmacologically acceptable salts.

7 Claims, No Drawings

3-SUBSTITUTED PENTANEDIOIC ACIDS AND DERIVATIVES THEREOF

BACKGROUND OF THE INVENTION (a) Field of the Invention

This invention in its broadest aspect relates to protease inhibitors. In one aspect, the invention relates to certain novel methods useful in preventing or treating disease states caused by the degradative action of proteases on mammalian elastin and other proteins by administration of effective amounts of compounds of Formula I. A preferred method relates to the inhibition of the proteases elastase and cathepsin G. In other aspect, it relates to compounds of Formula I which are useful in preventing or treating disease states caused by the degradative action of proteases on mammalian elastin and other proteins.

Elastin is the functional protein component of elastic fiber tissues, a component of connective tissues. Elastic tissue is relatively rich in elastin and has a distinct rubber-like property. Most specifically, the ligamentum nuchae and the vocal cords, the vertebral ligamenta flava, the aorta, and the pulmonary arteries of some mammals are considered elastic tissues. Elastic cartilaginous tissues such as those present in the ear and epiglottis are a specialized form of elastic tissue. Lung, bronchi and skin also contain elastin and are considered elastic tissue. Sandberg, et al., *New England Journal of Medicine*, Mar. 5, 1981, 566–579.

Elastase is an elastinolytic enzyme which causes degradation and fragmentation of elastic fibers by its catalytic activity against elastin. Elastases originate from a number of sources and can be found in microorganisms, snake venoms and a number of mammalian cells and tissues including pancreas, polymorphonuclear leukocytes, and macrophages. In a normally functioning mammal, elastase is required for turnover of damaged cells and the digestion of certain invading bacteria. This invention in particular relates to the class of elastases known as the Serine Proteases.

Excessive elastin degradation has been associated with pulmonary emphysema, adult respiratory-distress syndrome, arthritis, atherosclerosis, certain skin diseases, and certain inflammatory processes leading to localized protein breakdown. Werb, et al., *Journal of Investigative Dermatology*, 79:154S–159S, (1982); Rinaldo, et al., *New England Journal of Medicine*, 306:900–909, (1982). By inhibiting elastase therefore it is possible to mediate, eliminate or treat a wide variety of disease conditions.

A number of inhibitors of elastase are known. Peptide chloromethyl ketones have been shown to be irreversible inhibitors of elastase. But difficulties must be considered when the in vivo use of peptide chloromethyl ketones is contemplated. The compounds are electrophiles and can react with good nucleophiles such as the thiol groups of glutathione and various proteins. During any long term treatment with these inhibitors, such non-specific alkylation could lead to the introduction of new antigenetic determinants and an autoimmune response and/or could behave similarly to the known nitrogen mustards, etc. Peptides containing aza-amino acid residues (aza peptides) are another class of inhibitors. The effectiveness of aza-peptides as elastase inhibitors depends on the rate of acylation, which in most cases is instantaneous, and also on the rate of deacylation. As such, these compounds while useful tools in studying the in vitro properties of elastase are still largely unsuitable for in vivo use.

(b) Information Disclosure

The treatment of certain disease states by inhibitors of elastase is known as described above.

SUMMARY OF THE INVENTION

The present invention particularly provides compounds of formula 1:

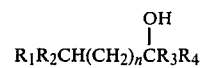

wherein $R_1$ is t-butyl and wherein $R_2$ is hydrogen, or wherein $R_1$ and $R_2$ are taken together to form a cyclohexyl group; wherein $R_3$ is $CH_2CO_2R_5$ and wherein $R_4$ is $CH_2CO_2H$, or wherein $R_3$ and $R_4$ are taken together to form a group as follows:

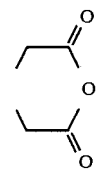

wherein $R_5$ is (a) hydrogen; or (b) alkyl of 1 to 6 carbon atoms inclusive;

wherein n is an integer such that the total number of carbon atoms in $R_1R_2CH(CH_2)_n$ totals 18 to 22.

Examples of alkyl of from 1 to 6 carbon atoms, inclusive, are methyl, ethyl, propyl, butyl, pentyl, hexyl and the isomeric forms thereof.

The compounds useful in practicing the method of the invention are inhibitors of leucocyte elastase and cathepsin G. Since elastase is involved in the breakdown of elastin and subsequently involved in a number of disease states, a compound which blocks the action of elastase will be useful in the management, treatment and prevention of such diseases. Elastase, in addition to degrading elastin, also will hydrolyse methoxysuccinyl-ala-ala-pro-val-nitroanalide (MSN), a highly selective synthetic substance. Kakajima, K., et al., *J. Biol. Chem.*, 254, 4027 (1979). This is useful in measuring inhibition of elastase because the hydrolysis of MSN is easily quantitated by measuring the release of p-nitroaniline spectrophotometrically. Therefore, the degree of elastase inhibition can be readily measured by noting the rate of inhibition of the hydrolysis of MSN. The compounds of the invention are therefore tested in vitro as follows. The rate of hydrolysis of methoxysuccinyl-ala-ala-pro-val-nitroanalide by human leukocyte elastase is monitored spectrophotometrically in the presence and absence of test compound. The inhibition of the enzymatic reaction by 20% or more is taken as positive inhibition. $IC_{50}$ values are then determined.

The following procedure is used to test the compounds in vivo (collagen-induced rat arthritis model). The method is based on that of Trentham, D. E., Townes, A. S. and Kang, A. H. in *J. Exp. Med.* 146, 857–968 and results are evaluated thereby.

Inbred female Wistar rats (200–230 G) were randomly assigned to 3 groups of 30 animals each. Arthritis was induced by intradermal injection of bovine nasal septum Type II collagen in incomplete Freunds adjuvant.

Drug treatment was oral, once daily in 0.5 ml carboxymethyl cellulose from day 0 until sacrifice:
Group 1: Test compound 50-100 mg/kg/day
Group 2: Phenylbutazone 40 mg/kg/day (positive control)
Group 3: 1% V/V carboxymethyl cellulose (negative control)

(1) Physical measurements of hind paws were made for (a) swelling across plantar region; (b) malleolar thickening; (c) extensibility of ankle joint. Results were subject to systematic statistical evaluation.

(2) Histological examination of hind paws were made in groups of 5 animals sacrificed at days 7, 14, 21 and 28. Sections were taken at 3 levels through each foot and examined for indication of disease progression.

During periods of active rheumatoid arthritis, vast numbers of human neutrophils are attracted to diseased joints where they engage in phagocytosis of locally generated immune complexes and tissue debris. During the process, enzymes (primarily elastase and cathepsin G) are released into the joint spaces. Elastase has the capacity in this situation to degrade synovial cartilage and collagen and contribute to joint destruction in a synergistic process with cathepsin G. Cathepsin G also causes conversion of angiotensin I to angiotensin II which is associated with inflammatory processes, Reilley, C. F., et al., *J. Biol. Chem.*, 257, 8619 (1982) and angiotensinogen to angiotensin II, Tonnesen, M. G., et al., *J. Clin. Invest.*, 69, 25 (1982). Natural elastase inhibitors (macro molecules such as in $\alpha_1$-proteinase inhibitor) already exist in normal serum and synovial fluid and may prevent precipitous joint destruction. Oxidation of the natural inhibitor (to the sulfoxide form) renders this material inactive. Wong, P. S. and J. Travis, *Biochem Biophys. Res. Commun.*, 96, 1449 (1980). Exogenous smaller molecular weight inhibitors of the invention can gain access to the micro-environments within the joint space not accessible to the natural inhibitors due to their molecular size, oxidation, charge repulsion or lipid solubility, and thereby inhibit or prevent further elastase-related destruction. In addition, pulmonary emphysema is a disease characterized by a progressive uninhibited proteolysis of lung tissue by enzymes such as elastase which in this case are released from leukocytes. People who are homozygotes in an $\alpha_1$-antitrypsin deficiency are predisposed to the disease. See, e.g., Turimo, et al., *Amer. J. Med.*, Vol. 57, pp. 493-503 (1974). The compounds of the invention could also be used to prevent the further proteolysis of lung tissue. Again, the ability of the compounds to inhibit cathepsin G is desirable, since the combination of elastase and cathepsin G has been reported to be five times as efficient at degrading elastin as is elastase alone. Boudier, C., et al., *J. Biol. Chem.* 256, 10256 (1981). In a like manner, adult respiratory-distress syndrome, certain skin diseases, aging, and certain inflammatory processes where the disease state is connected with the localized breakdown of protein by elastase could be treated by elastase inhibitors, such as the compounds of this invention. For example, degradation of fibronectin, an important biological substance, could be inhibited. McDonald, J. A., and D. G. Kelley, *J. Biol. Chem.*, 255, 8848 (1980). The compounds may also be useful in the treatment of other enzyme related diseases, such as fribrosis related to prolyhydroxylase, and the like. This invention is not limited to these examples as one skilled in the art could readily apply these methods to any protease related disease or condition.

The method of the invention can be practiced in a variety of ways and the compounds can be administered in a number of dosage forms. A preferred method of delivery would be in such a manner so as to localize the action of the inhibitor. So, for example, in arthritis, the compounds could be injected directly into the affected joint, or for emphysema, the compounds could be inhaled using an aerosol or other appropriate spray. In any event, the compounds may be administered in any conventional manner. The compounds could be administered in oral unit dosage forms such as tablets, capsules, pills, powders or granules. They also may be administered rectally or vaginally in such forms as suppositories. They may be introduced in the forms of eyedrops, intraperitoneally, subcutaneously, or intramuscularly using forms known to the pharmaceutical art. For the treatment of inflammatory skin diseases, the compounds of the present invention may also be administered topically in the form of ointments, creams, gels or the like. Regardless of the route of administration selected, the compounds are formulated into pharmaceutically acceptable dosage forms by conventional methods known to the pharmaceutical art.

An effective but non-toxic quantity of the compound is employed in treatment. The dosage regimen for elastase inhibition by the compounds of this invention is selected in accordance with a variety of factors including the type, age, weight, sex, and medical condition of the mammal, the particular disease and its severity, the route of administration and the particular compound employed.

An ordinarily skilled physician or veterinarian will readily determine and prescribe the effective amount of the compound to prevent or arrest the progress of the condition. In so proceeding, the physician or veterinarian could employ relatively low dosages at first, subsequently increasing the dose until a maximum response is obtained.

The general procedure for producing the compounds of the instant invention is outlined on Chart A. It is similar to the general procedure used to produce the compounds of U.S. Pat. No. 3,818,080 and U.S. Ser. No. 360,543, now abandoned, herein incorporated by reference.

The invention will appear more fully from the Examples which follow. These Examples are given by way of illustration only and are not to be construed as limiting the invention either in spirit or in scope, as many modifications both in materials and methods will be apparent from this disclosure to those skilled in the art. In these examples, temperatures are given in degrees celcius (°C.) and quantities of materials in grams and milliliters unless otherwise noted.

DESCRIPTION OF THE PREFERRED EMBODIMENTS

The operation of this invention is further elaborated by the representative examples below:

EXAMPLE 1

13,13-dimethyl tetradecanol t-butyl(CH$_2$)$_{12}$OH

To 7.2 g. of lithium aluminum hydride suspenced in 800 ml dry ethyl ether was added dropwise with stirring under nitrogen a solution of 51.6 g of methyl 13,13-dimethyl tetradecanoate in 200 ml of ether. After stirring and refluxing for 4 hours, the mixture was decomposed with ethanol, then with water, then acidified with dilute HCl. After extraction, the ether layer was separated, washed twice with water, dried with anhydrous potassium carbonate and evaporated. Distilation of the residue afforded the product as a water-white oil, b. 123°–125°/0.5 mm, 44.7 g. tlc (90:10 by volume Skellysolve B/ethyl acetate) using Merck silica gel: $R_f$ ca. 0.3.

Infrared (CHCl$_3$): ca. 1640 cm$^{-1}$(hydroxyl), ca. 2860, 2940 cm$^{-1}$(alkane).

nmr(CDCl$_3$)[δ, ppm]: 0.87 (s, t-Bu), 1.2–1.7(m, methylene, 3.65 (t, —CH$_2$O—).

Elemental: Calcd. for C$_{16}$H$_{34}$O: C, 79.26; H,14.14; Found: C, 79.29; H, 13.94.

EXAMPLE 2

13,13-dimethyl tetradecanal t-butyl (CH$_2$)$_{11}$ CHO

The alcohol from Example 1, 24.2 g., and 41.4 g of pyridinium dichromate were stirred overnight in 700 ml of methylene chloride. The suspension was filtered, the filtrate was concentrated in vacuo and then passed through a short column of Fluorosil to remove traces of chromium salts. The eluate was evaporated and the residue distilled to yield the product as a water-white oil, b. 116°–118°/0.4 mm, 17.4 g.

Infrared (CHCl$_3$): ca. 1720 cm$^{-1}$(carbonyl), ca. 2860, 2930 cm$^{-1}$(alkane).

nmr(CDCl$_3$)[δ, ppm]: 0.87 (s, t-Bu), 1.15–1.5(m, alkane, 2.45 (t, —CH$_2$CHO).

Elemental: Calcd. for C$_{16}$H$_{32}$O: C, 79.93; H, 13.42; Found: C, 79.54; H, 13.36.

EXAMPLE 3

19,19-dimethyleicos-6-enoic acid t-butyl (CH$_2$)$_{11}$ CH=CH(CH$_2$)$_4$CO$_2$H A solid suspension of 50% NaH in mineral oil, 6.3 g, was washed and filtered under nitrogen with three portions of dry tetrahydrofuran (THF). To the damp solid remaining was added 100 ml of dimethyl sulfoxide (DMSO) and the suspension was stirred and warmed to 60° for ½ hour until evolution of hydrogen ceased. The mixture was cooled to 20°–25° and a solution of 27.4 g of 6-triphenylphosphonium hexanoic acid bromide in 100 ml of DMSO was added dropwise with stirring. The mixture was diluted with 200 ml THF and cooled to 0°–5°. While stirring a solution of 17.0 g of the product in Example 2 in 100 ml of THF was added rapidly, then the mixture was stirred overnight while the ice-cooling bath slowly warmed to room temperature.

The reaction mixture was decomposed with water, made strongly acid with dilute sulfuric acid, then extracted twice with Skellysolve B. These extracts were combined, washed thoroughly (4 times) with dilute sulfuric acid (until triphenylphosphine oxide no longer separated as an insoluble oil), then dried and the solvent evaporated to yield the product as a yellow oil, 21.9 g, which was used without purification in the next step.

EXAMPLE 4

Methyl 19,19-dimethyleicos-6-enoate t-butyl (CH$_2$)$_{11}$ CH=CH(CH$_2$)$_4$CO$_2$Me The oil from Example 3 was dissolved in 400 ml of methanol containing 1 ml of thionyl chloride and the solution allowed to stand for 3 hours. The solvent was evaporated in vacuo, the residue when taken up in ether was washed with dilute sodium bicarbonate. After drying, the solvent was evaporated and the residue distilled twice to yield the product as a water-white oil, b. 162°–167°/0.1 mm, 9.2 g.

tlc, (90:10 by volume Skellysolve B/ethyl acetate) using Merck silica gel: $R_f$ ca. 0.7.

Infrared (CHCl$_3$): ca. 1730 cm$^{-1}$(carbonyl), 2860, 2940 cm$^{-1}$(alkane).

nmr(CDCl$_3$)[δ, ppm]: 0.87 (s, t-Bu), 1.15–2.5 (m, alkylene), 3.68 (s,CH$_3$O—) 5.25—5.5 (m, vinyl).

Elemental: Calcd. for C$_{23}$H$_{44}$O$_2$: C, 78.37; H,12.58; Found: C, 77.87; H, 12.63.

EXAMPLE 5

4 Methyl 19,19-dimethyleicosanoate t-butyl (CH$_2$)$_{17}$ CO$_2$Me

Hydrogenation of 8.9 g of the unsaturated ester from Example 4 was effected in THF at room temperature under 2 psi hydrogen using 5%. palladium on carbon as catalyst. After filtration the solvent was evaporated and the residue distilled to furnish the product as a water-white oil, 7.45 g, b. 167°–170°/0.25 mm, which crystallized on standing.

Infrared (CHCl$_3$): ca. 1740 cm$^{-1}$ (carbonyl, 2860, 2930 cm$^{-1}$ (alkane).

nmr(CDCl$_3$)[δ, ppm]: 0.87 (s, t-Bu),1.15–1.4 (m, alkylene), 2.30 (t, —CH$_2$CO), 359 (s, CH$_3$O—).

Elemental: Calcd. for C$_{23}$H$_{46}$O$_2$: C, 77.90; H,13.08; Found: C, 78.04; H, 13.37.

EXAMPLE 6

1,1-Bis(allyl)19,19-dimethyleicosanol

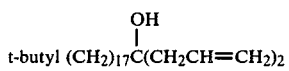

To a stirred suspension of 1.11 g of magnesium shavings in 250 ml dry THF under nitrogen was added 0.5 ml of allyl bromide, 0.5 ml of 1 M allyl magnesium bromide in ether, and a catalytic amount of iodine. When the reaction started a solution of 5.53 g of allyl bromide and 7.05 g of the product from Example 5 in 50 ml THF was added dropwise at reflux. The mixture was stirred and refluxed 1 hour, then cooled, decomposed with methanol, and diluted with ether. This solution was washed well with a saturated solution of ammonium chloride, then dried and the solvent evaporated in vacuo to yield the product as a yellow oil, 9.33 g, which was used without further purification.

tlc, (90:10 by volume Skellysolve B/ethyl acetate) using Merck silica gel: $R_f$ ca. 0.5.

EXAMPLE 7

3-(18,18-dimethylnonadecyl)-3-hydroxyglutaric acid

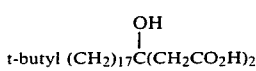

Ozone was bubbled into a solution cooled at −60° to −70° of 9.3 g of the product in Example 6 dissolved in 300 ml of 1:1 (by volume) methylene chloride/ethylacetate until a blue color persisted-ca. ½ hour. One portion of 100 ml of glacial acetic acid was added and while stirring, the solution was heated to an internal temperature of 77° while distilling off most of the methylene chloride. A solution of 20 ml of water, 40 ml of 10% (w/w) of sulfuric acid, 60 ml of glacial acetic acid and 40 ml of 30% hydrogen peroxide was added, and again stirred and distilled until the internal temperature reached 85°. After refluxing 2 hours, the solution was cooled, stripped in vacuo to near dryness, diluted with water, and extracted twice with ether. The ether extracts were combined, washed three times with dilute sulfuric acid, then extracted twice with dilute sodium hydroxide. These extracts were combined, dilute sodium bisulfate added until no peroxide remained on starch-iodide test, then acidified with dilute sulfuric acid and extracted with ether. Ths ether extract was washed with dilute sulfuric acid, then dried and evaporated to yield the product as a white powder, 6.1 g. tlc, (50:48:2 (by volume) toluene/ethyl acetate/acetic acid) using Merck silica gel: $R_f$ ca. 0.6.

Infrared (CHCl$_3$): ca. 1720 cm$^{-1}$ with shoulder at 1750 cm$^{-1}$ (carboxyl), 2860, 2940 cm$^{-1}$ (alkane) 3500 cm$^{-1}$ (hydroxyl).

nmr(CDCl$_3$)[δ, ppm]: 0.88 (s, t-Bu), 1.15–1.7 (m, alkylene), 3.27 (broad s, —CH$_2$CO$_2$H).

Elemental: Calcd. for C$_{26}$H$_{50}$O$_5$: C, 70.54; H,11.39; Found: C, 70.31; H, 11.45.

EXAMPLE 8

3-(18,18-dimethylnonadecyl)-3-hydroxyglutaric anhydride

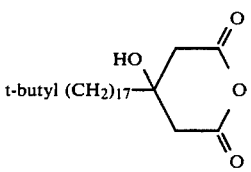

To 3.99 g of the product from Example 7 dissolved in 200 ml of 30% (v/v) of acetone-methylene chloride was added 2.05 g of dicyclohexylcarbodiimide. After standing overnight the precipitate of dicyclohexylurea was filtered off and the filtrate evaporated to dryness. The residue was dissolved in ether, stirred for 2 hours with dilute AcOH, the ethyl layer was separated, filtered to remove dicyclohexyl urea, dried, and evaporated. The residue was crystallized from 40 ml of acetonitrile at 0° to furnish the product as white prisms, 2.96 g.

tlc, (ethyl acetate) using Merck silica gel: $R_f$ ca. 0.9.

Infrared (CHCl$_3$): ca. 1760, 1820 cm$^{-1}$ (anhydride) 2850, 2920 cm$^{-1}$ (alkane), 3520 cm$^{-1}$ (hydroxyl).

nmr(CDCl$_3$) [δ, ppm]: 0.88 (s, t-Bu), 1.15–1.8 (m, alkylene), 2.72–2.90 (m, —CH$_2$CO—).

Elemental: Calcd. for C$_{26}$H$_{48}$O$_4$: C, 73.54; H,11.39; Found: C, 73.71; H, 11.64.

EXAMPLE 9

3-(18,18-dimethylnonadecyl)-3-hydroxyglutaric acid monomethyl ester

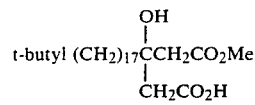

A solution of 0.501 g of the anhydride (Example 8) and 0.124 g of 4-dimethylaminopyridine in 125 ml of methanol was refluxed 2 hours, and then allowed to stand overnight at room temperature. The solvent was evaporated in vacuo, and the residue taken up in ether was washed with dilute HCl, then the solution was dried, concentrated, and diluted with Skellysolve B. On cooling, the product crystallized as white, matted needles, 0.47 g.

Infrared (CHCl$_3$): ca. 1700, shoulder 1740 cm$^{-1}$ (carbonyl), 2850, 2920 cm$^{-1}$ (alkane), 3500 cm$^{-1}$ (hydroxyl).

nmr(CDCl$_3$)[δ, ppm]: 0.86 (s, t-Bu), 1.05–1.75 (alkylene), 2.67 (s, —CH$_2$CO—), 3.72 (s, CH$_3$O—).

Elemental: Calcd. for C$_{27}$H$_{52}$O$_5$: C, 71.00; H,11.44; Found: C, 71.03; H, 11.29.

EXAMPLE 10

3-(15-cyclohexylpentadecyl)-3-hydroxyglutaric acid monomethyl ester

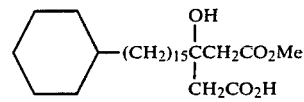

By substituting 5-phenylpentanol for 13,13-dimethyltetradecanol in Example 2, and 11-triphenylundecanoic acid bromide for the named bromide in Example 3, then carrying out the sequence of Examples 2 through 4 using proportionate molar quantities of reactants, methyl 16-phenylhexadec-11-enoate is obtained. When this material is hydrogenated with four moles of hydrogen at 60 psi in THF at 80° using 5% rhodium on carbon as catalyst, both the chain double bond and the phenyl ring are saturated, yielding methyl 16-cyclohexylhexadecanoate as a water-white, high boiling oil. Reaction of this material as Example 6 through 9 affords the title compound as a white powder.

CHART A

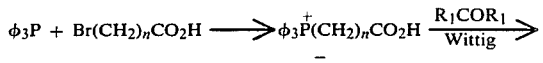

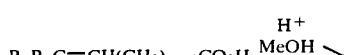

II

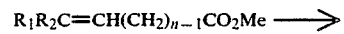

III

-continued
CHART A

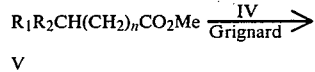

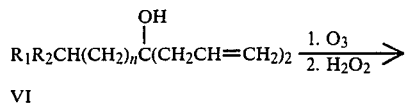

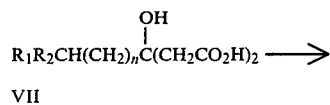

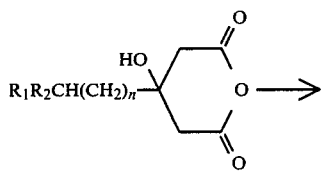

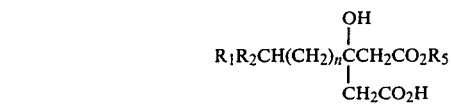

Where:
R₁ is t-Bu, or combined with R₂ to form cyclohexyl;
R₂ is H, or combined with R₁ as above.

What is claimed is:

1. A compound of the formula:

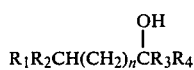

wherein $R_1$ is t-butyl; wherein $R_2$ is hydrogen; wherein $R_3$ is $CH_2CO_2R_5$ and wherein $R_4$ is $CH_2CO_2H$, or wherein $R_3$ and $R_4$ are taken together to form a group as follows:

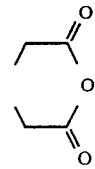

wherein $R_5$ is:
(a) hydrogen; or
(b) alkyl of 1 to 6 carbon atoms, inclusive; and
wherein n is an integer such that the total number of carbon atoms in $R_1R_2CH(CH_2)_n$ totals 18 to 22.

2. A compound according to claim 1 of the formula:

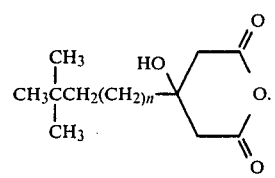

3. 3-(18,18-dimethylnonadecyl)-3-hydroxyglutaric acid, a compound according to claim 2.

4. A compound according to claim 1 of the formula:

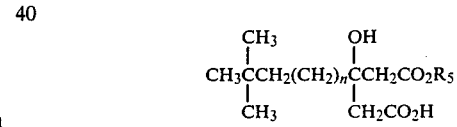

5. 3-(18,18-dimethylnonadecyl)-3-hydroxyglutaric anhydride, a compound according to claim 4.

6. A compound according to claim 1 of the formula:

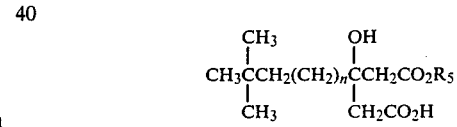

wherein $R_5$ is alkyl of 1 to 6 carbon atoms, inclusive.

7. 3-(18,18-dimethylnonadecyl)-3-hydroxyglutaric acid monomethyl ester, a compound according to claim 6.

* * * * *